United States Patent [19]
Riley

[11] Patent Number: 5,573,741
[45] Date of Patent: Nov. 12, 1996

[54] SURGICAL INSTRUMENT STERILIZATION CONTAINER WITH IMPROVED LATCHING MECHANISM

[76] Inventor: Edward D. Riley, 16 Brookside Dr., Falmouth, Me. 04105

[21] Appl. No.: 492,712

[22] Filed: Jun. 20, 1995

[51] Int. Cl.⁶ ............................. A61L 2/20; B65D 45/16
[52] U.S. Cl. .................. 422/300; 422/297; 206/439; 220/324
[58] Field of Search ........................... 422/292, 297, 422/300; 206/439; 220/324; 292/288, 258, 80, DIG. 30

[56] References Cited

U.S. PATENT DOCUMENTS

| | | | |
|---|---|---|---|
| D. 339,424 | 9/1993 | Riley | D24/217 |
| 3,181,726 | 5/1965 | Parker | 220/324 |
| 3,390,806 | 7/1968 | Herbert | 220/324 |
| 3,612,335 | 10/1971 | Schurman | 220/324 |
| 4,643,303 | 2/1987 | Arp et al. | 206/370 |
| 4,661,326 | 4/1987 | Schainholz | 206/439 |
| 4,671,943 | 6/1987 | Wahlquist | 422/300 |
| 4,748,003 | 5/1988 | Riley | 422/112 |
| 4,798,292 | 1/1989 | Hauze | 206/439 |
| 4,820,499 | 4/1989 | Taschner | 422/300 |
| 4,854,475 | 8/1989 | Riihimaki et al. | 220/337 |
| 4,915,913 | 4/1990 | Williams et al. | 422/300 |
| 5,084,251 | 1/1992 | Thomas | 422/300 |
| 5,098,676 | 3/1992 | Brooks, Jr. | 422/292 |
| 5,125,697 | 6/1992 | Kahl et al. | 222/324 |
| 5,165,539 | 11/1992 | Weber et al. | 206/363 |
| 5,297,692 | 3/1994 | Kronmiller | 292/258 |

FOREIGN PATENT DOCUMENTS

| | | |
|---|---|---|
| 3534897 | 4/1987 | Germany . |
| 4103146 | 3/1992 | Germany . |

*Primary Examiner*—Robert J. Warden
*Assistant Examiner*—Theresa T. Snider
*Attorney, Agent, or Firm*—Cesari and McKenna

[57] ABSTRACT

A container for the sterilization of articles disposed therein, including surgical instruments, having a base unit and a matching cover unit. A locking mechanism, including a C-shaped tab, is pivotally and removably attached to each end of the base unit so that each tab can pivot between an open and a locked position. Each tab includes a first locking ridge located on an upper portion of the tab. The cover unit includes a second locking ridge located at each end of the cover unit for interfitting with the first locking ridge of the corresponding tab when the tab is in the locked position.

7 Claims, 4 Drawing Sheets

SURGICAL INSTRUMENT STERILIZATION CONTAINER WITH IMPROVED LATCHING MECHANISM

FIELD OF THE INVENTION

This invention relates to containers for articles to be sterilized by exposure to steam. More specifically, this invention relates to improvements in the latching mechanism for securing the cover unit of a sterilization container to the base unit.

BACKGROUND OF THE INVENTION

Sterilization of surgical instruments and the like is often performed in an autoclave where the instruments are exposed to steam at an elevated temperature. The instruments are disposed in a container having a cover unit and a base unit. The surfaces of the cover unit and the base unit are perforated to permit the steam to pass therethrough. The perforations also ensure that the instruments disposed within the container will be exposed to the hot steam immediately upon their introduction into the autoclave.

When transporting the container, it is important that the cover unit of the container be securely attached to the base unit supporting the instruments. Failure of the cover to remain securely attached to the base can result in the sterilized instruments being dropped during removal or transport from the autoclave, possibly contaminating the instruments. It is also important that the cover unit be easily removed from the base unit in order to quickly access the sterilized instruments in the container.

SUMMARY OF THE INVENTION

Accordingly, it is an object of the present invention to provide a surgical sterilization container with an improved latching mechanism which securely attaches the cover unit of the container to the base unit.

Another object of the invention is to provide an improved latching mechanism which permits quick and easy operation in order to reduce the time necessary to open the container and remove the sterilized instruments disposed therein.

A sterilization container incorporating the invention has two ends and comprises a cover unit which can be removably attached to a base unit. At each end of the cover unit is a catch to be used in securing each end of the cover unit to the corresponding end of the base unit. The cover unit may also include a recess at each end, the recess having a floor and a back wall. The catch may be located along the floor of each recess in the cover unit. The cover unit and base unit may also be perforated, to permit the steam from the autoclave to pass through the container and across the instruments disposed therein.

The container further comprises a latching mechanism at each end of the container for securing the cover unit to the base unit. Each latching mechanism comprises a generally C-shaped tab pivotally and removably attached to each end of the base unit such that the tab can pivot from an open to a locked position. Each tab includes a locking ridge located at an upper portion of the tab. The locking ridge is adapted for interfitting with the corresponding catch at each end of the cover unit, when the tab is in the locked position, thereby securing the cover unit to the base unit. Each tab may also include a gripping flange for releasing the tab from its locked position on the cover unit.

The cover unit may also include a notch at the back wall of each recess. Each notch is adapted to permit a person's finger to release the tab from its locked position quickly and easily, by moving the gripping flange outwardly from the container.

DESCRIPTION OF THE PREFERRED EMBODIMENT

Figure 1:
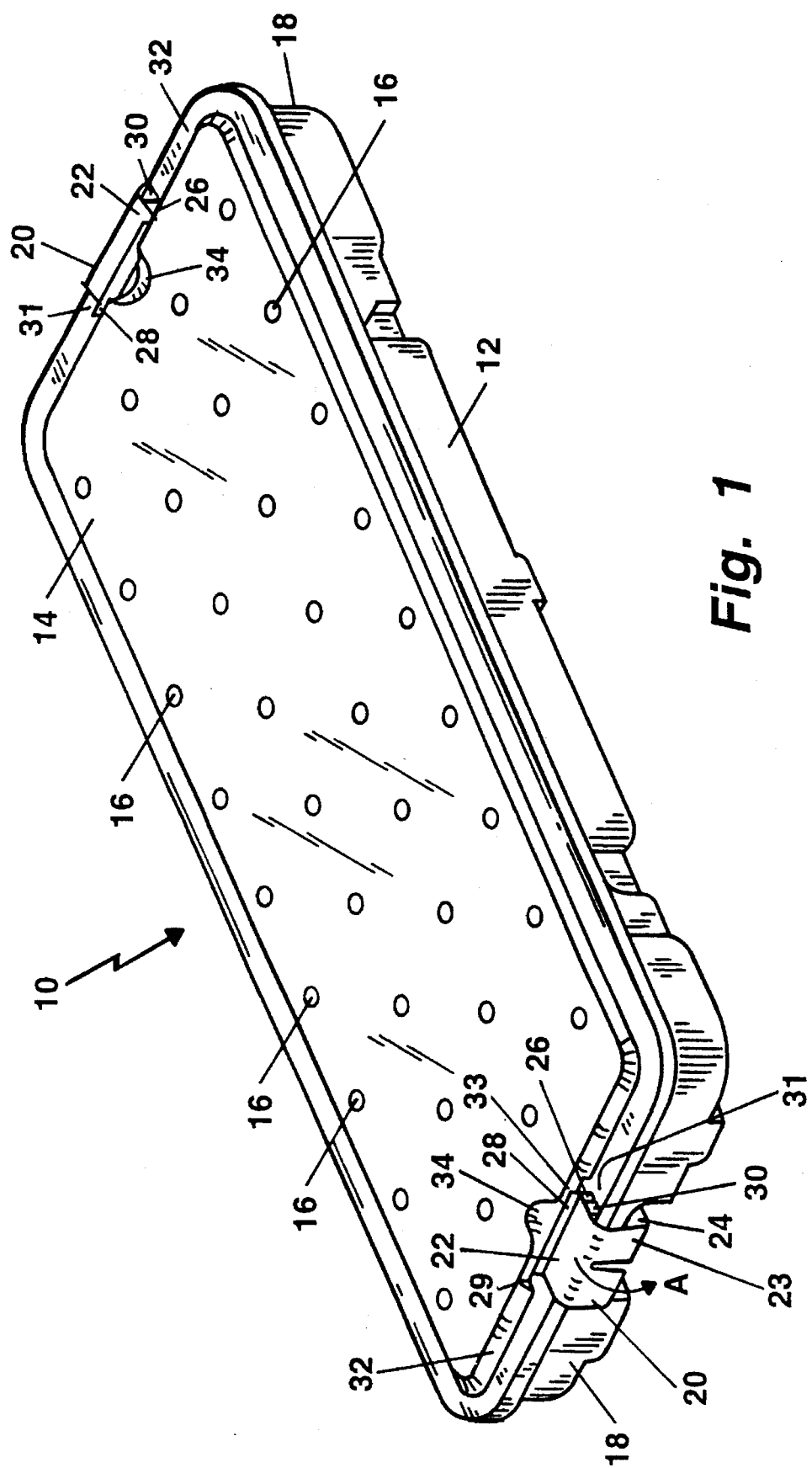
FIG. 1 is a front perspective view of a surgical instrument sterilization container incorporating the improved latching mechanism according to the invention showing the latching mechanism in the locked position.

As shown in FIG. 1, a generally rectangular sterilization container 10 comprises a base unit 12 and a cover unit 14 removably attached to the base unit 12. The base unit 12 and the cover unit 14 define an interior space 11 (FIG. 4) for the sterilization of articles (not shown) disposed within the interior space 11 of the container 10. The cover unit 14 and the base unit 12 have holes 16 so that steam from an autoclave (not shown) can pass through the container 10 thereby sterilizing the articles placed therein.

The base unit 12 has two end walls 18. Each end wall 18 of the base unit 12 includes two slots 44. The slots 44 are colinear and extend completely through the base unit 12. Each end wall 18 may further include an indentation 38 (FIG. 4), extending into the interior 11 of the container 10. The slots 44, corresponding to each end wall 18 of the base unit 12, may be located at the indentation 38.

Figure 5:
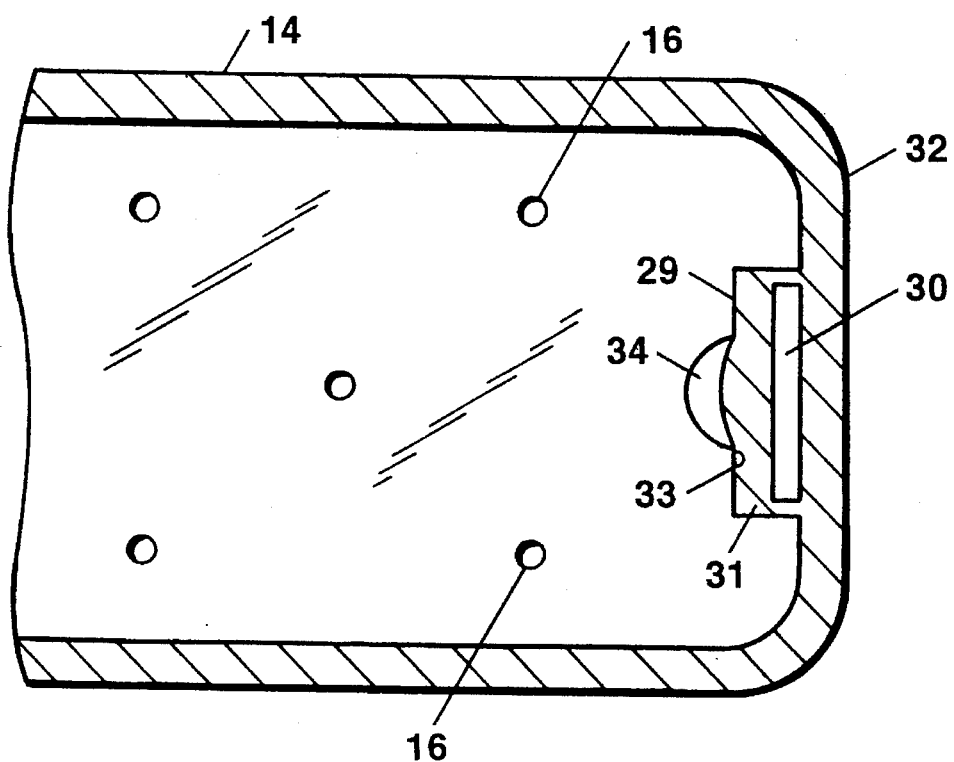
FIG. 5 is a partial top view of the cover unit of the surgical instrument sterilization container according to the invention.

The cover unit 14 has two ends 32. A recess 29 may be formed at each end 32 of the cover unit 14 (FIG. 5). Each recess 29 has a floor 31 and a back wall 33. Each end 32 of the cover unit 14 includes a catch 30, which may be semi-circular in cross-section. The catch 30 may be located along the floor 31 of each recess 29. The container 14 may further include a notch 34 at the back wall 33 of each recess 29. Each notch 34 is sized to fit the end of a person's finger (not shown).

Figure 2B:
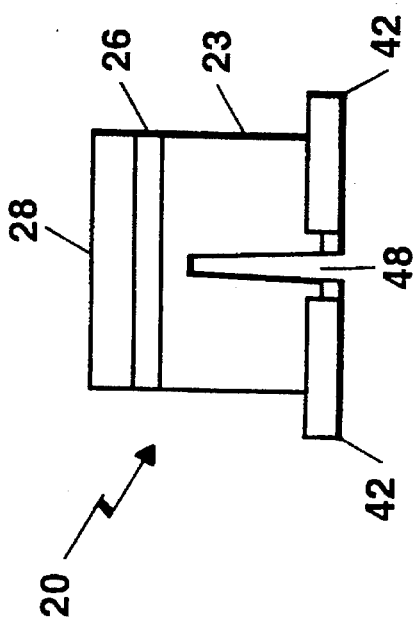
FIG. 2B is a front elevational view of the latching mechanism of FIG. 2A.
Figure 2C:
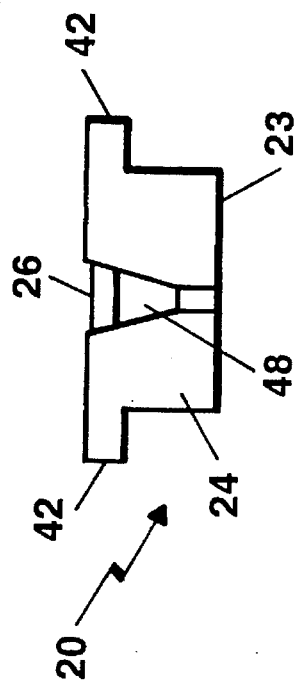
FIG. 2C is a bottom elevational view of the latching mechanism of FIG. 2A.
Figure 2A:
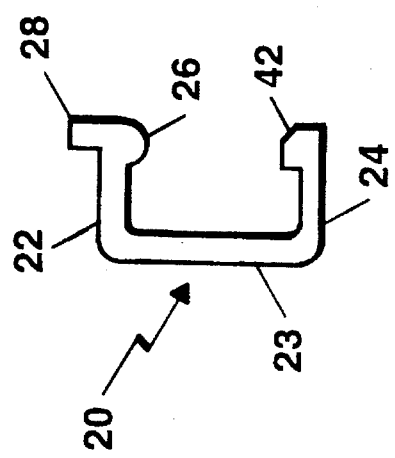
FIG. 2A is a side elevational view of a portion of the latching mechanism of the invention.

As shown in FIG. 1, a latch mechanism in the form of a C-shaped tab 20 is pivotally and removably attached to each end wall 18 of the base unit 12. Each tab 20 has an upper portion 22, a center portion 23 and a lower portion 24 (FIGS. 2A–2C). The upper portion 22 of each tab 20 is adapted to fit into the corresponding recess 29 at each end 32 of the cover unit 14.

Figure 3:
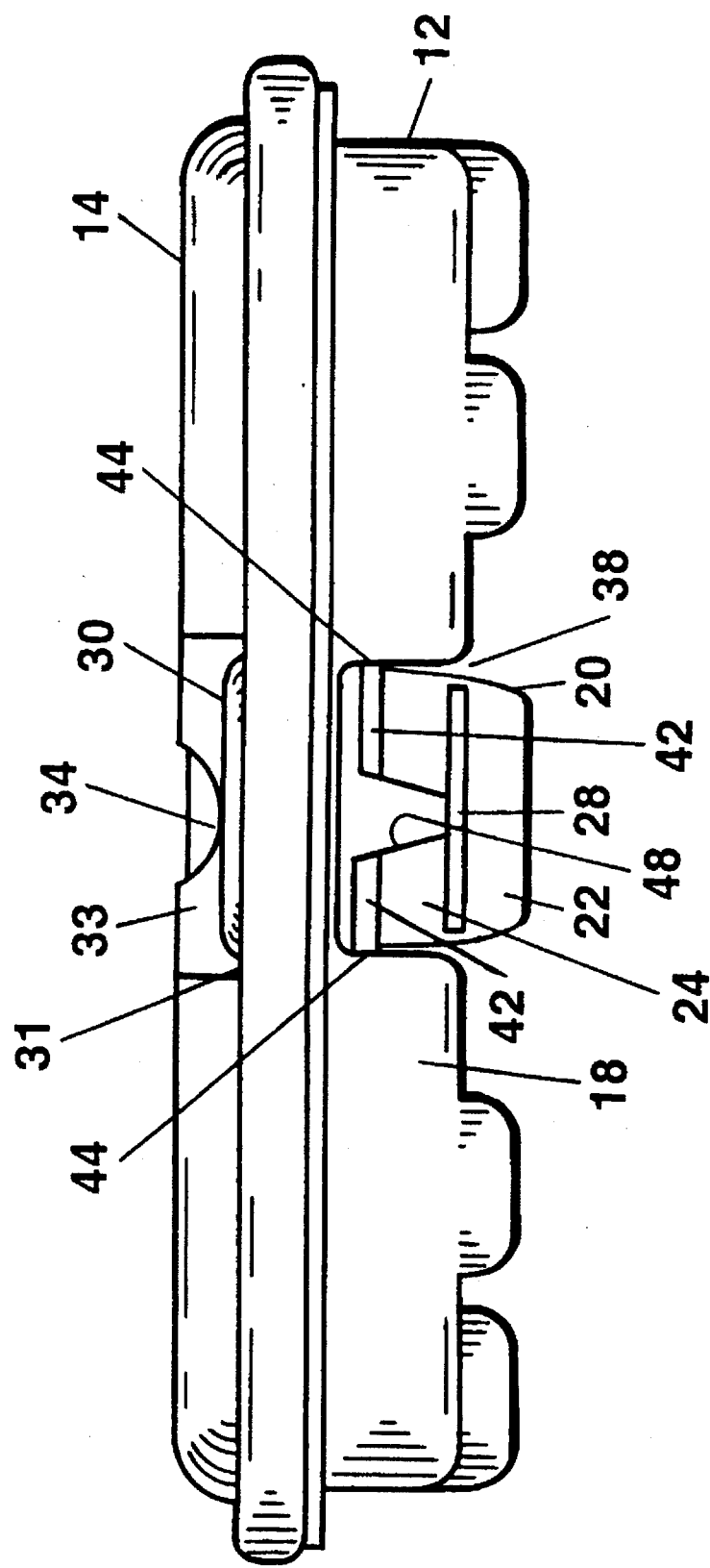
FIG. 3 is a side elevational view of the container with the latching mechanism in the open position.

A locking ridge 26 is located on the inside face of each tab 20 at the upper portion 22 (FIG. 3A). The locking ridge 26, which may be semi-circular in cross-section, may extend the entire width of the tab 20. The locking ridge 26 is adapted for interfitting with the corresponding catch 30 of each end 32 of the cover unit 14, when the tab 20 is in the locked position. Each locking ridge 26 may extend parallel to the corresponding catch 30, when the tab 20 is in the locked position.

As shown in FIGS. 2A and 2B, each tab 20 may further include a gripping flange 28, which extends perpendicularly from the tab 20 at the upper portion 22.

Figure 4:
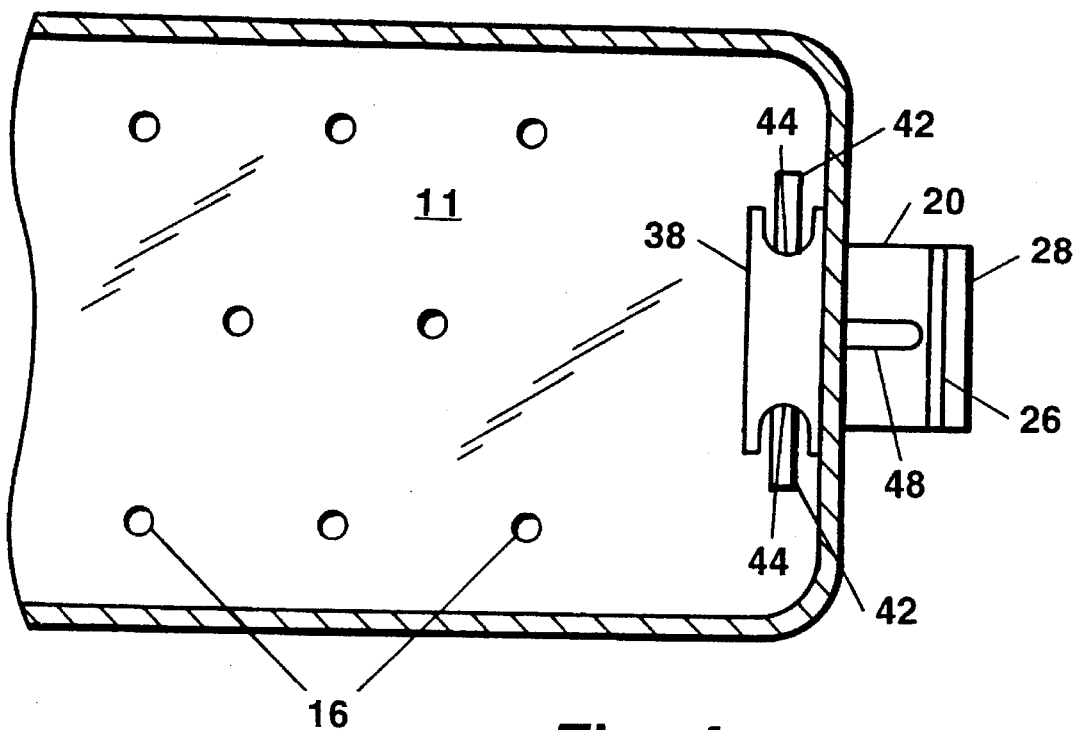
FIG. 4 is a partial top view of the container of FIG. 3 with the cover unit removed.

Each tab 20 further includes two pivot studs 42 at the lower portion 24 of the tab 20. The pivot studs 42 extend outwardly from the tab 20 and may be colinear. As shown in FIG. 4, the pivot studs 42 are adapted to fit into the corresponding slots 44 at each end wall 18 of the base unit 12. The pivot studs 42 extend through the slots 44 into the interior 11 of the base unit 12, allowing the tab 20 to rotate about the pivot studs 42. Preferably, the pivot studs 42 extend sufficiently into the interior 11 of the base unit 12 such that the tab 20 is prevented from inadvertently slipping out of the base unit 12.

As shown in FIGS. 2B and 2C, each tab 20 further includes a slit 48 extending along a vertical axis of the tab 20 from the base portion 24 to the center portion 23. The slit 48 is preferably widest at the base portion 24 and decreases in width as the slit 48 reaches the center portion 23 of the tab 20. The width of the slit 48 is constant as it extends along the vertical axis of the center portion 23 of the tab 20.

To secure the cover unit 14 to the base unit 12, each tab 20 is moved to the locked position on the corresponding end 32 of the cover unit 14. Each tab 20 is rotated so that the upper portion 22 of the tab 20 is received in the corresponding end 32 of the cover unit 14. The upper portion 22 of each tab 20 is then flexed upwardly as the locking ridge 26 passes over the corresponding catch 30. Once the locking ridge 26 passes over the catch 30, the upper portion 22 of each tab 20 snaps down toward the floor 31 of the corresponding recess 29. The catch 30 is of sufficient height to retain the tab 20 in the locked position by preventing the locking ridge 26 from passing back over the catch 30.

To open the container 10, each tab 20 is moved to its open position so that the cover unit 14 may be removed from the base unit 12. Each tab 20 is unlocked by pushing the gripping flange 28 outwardly from the corresponding notch 34 until the locking ridge 26 is disengaged from the corresponding catch 30. The locking ridge 26 is disengaged from the corresponding catch 30 by flexing the upper portion 22 of each tab 20 upwardly so that the locking ridge 26 may pass over the corresponding catch 30. Once the locking ridge 26 is disengaged from the catch 30, the tab 20 pivots outwardly as shown by arrow A (FIG. 1) and the cover unit 14 can be easily removed from the base unit 12 to access the articles disposed therein.

As shown in FIG. 4, the slit 48 is adapted to permit the removal of each tab 20 from each end wall 18 of the base unit 12, by allowing the pivot studs 42 of each tab 20 to be squeezed together, from the interior 11 of the base unit 12. The pivot studs 42 are squeezed together until the pivot studs 42 pass through the corresponding slots 44, thereby releasing the tab 20 from the base unit 12.

Preferably, the tab 20 is formed by injection molding from polyphenylsulfome, which gives the tab 20 sufficient rigidity to secure the cover unit 14 to the base unit 12, when each tab 20 is in the locked position, while still permitting each tab 20 to be moved to the open position quickly and easily by pushing the gripping flange 26 outwardly.

What is claimed is:

1. A container comprising:

a base unit forming a bottom of said container and having a wall;

a cover unit forming a top of said container and having an end and a first locking means located at the end; and a generally C-shaped tab having an upper portion and a lower portion separated by a center portion, the upper portion having a second locking means for interfitting with the first locking means and the lower portion including an edge, a notch extending inwardly from the edge and two collinear pivot studs projecting from the edge in opposite directions, wherein the wall of said base unit comprises an indentation constructed to receive the lower portion of the tab, the indentation having two spaced-apart, collinear slots such that the edge of the tab may be positioned between the slots with the pivot studs being received in the slots thereby allowing the tab to pivot between a locked position in which the second locking means interfits with the first looking means and an open position in which the second locking means is spaced from the first locking means, and further wherein the tab is capable of being removed from the base unit by squeezing the two pivots studs together as provided by the notch so that the pivot studs may be removed from the corresponding slots in the indentation.

2. The container of claim 1 further comprising a flange extending perpendicularly from the upper portion of said tab opposite the second locking means.

3. The container of claim 2 wherein said cover unit further comprises a rounded notch located at the end of said cover unit, the notch proximate to and facing the flange of the C-shaped tab when the tab is in the locked position, the notch constructed to receive a person's finger for moving the corresponding tab from the locked position to the open position by pushing the flange away from said cover unit.

4. The container of claim 1 wherein the first locking means comprises a locking ridge and the second locking means comprises a catch.

5. The container of claim 4 wherein the ridge has a semicircular cross-section and the catch has a semicircular cross-section.

6. A surgical instrument sterilization container for use in a steam autoclave, said container comprising:

a base unit forming a bottom of said sterilization container and having a wall, the base unit perforated to permit steam from the autoclave to pass through the base unit;

a cover unit forming a top of said sterilization container and having an end and a first locking means located at the end; and a generally C-shaped tab having an upper portion and a lower portion separated by a center portion, the upper portion having a second locking means for interfitting with the first locking means and the lower portion including an edge, a notch extending inwardly from the edge and two collinear pivot studs projecting from the edge in opposite directions, wherein the wall of said base unit comprises an indentation constructed to receive the lower portion of the tab, the indentation having two spaced-apart, collinear slots such that the edge of the tab may be positioned between the slots with the pivot studs being received in the slots thereby allowing the tab to pivot between a locked position in which the second locking means interfits with the first looking means and an open position in which the second locking means is spaced from the first locking means, and further wherein the tab is capable of being removed from the base unit by squeezing the two pivots studs together as provided by the notch so that the pivot studs may be removed from the corresponding slots in the indentation.

7. The surgical instrument container of claim 6 wherein said base unit has two opposing end walls, said cover unit has two opposing ends and said container further comprises two C-shaped tabs one at each end wall of said base unit.

* * * * *